US00PP16407P3

(12) United States Plant Patent
Austin

(10) Patent No.: US PP16,407 P3
(45) Date of Patent: Apr. 4, 2006

(54) SHRUB ROSE PLANT NAMED 'AUSCHESNUT'

(50) Latin Name: *Rosa hybrida*
Varietal Denomination: AUSchesnut

(75) Inventor: David C. H. Austin, Wolverhapton (GB)

(73) Assignee: David Austin Roses Limited, Wolverhapton (GB)

( * ) Notice: Subject to any disclaimer, the term of this patent is extended or adjusted under 35 U.S.C. 154(b) by 115 days.

(21) Appl. No.: 10/944,058

(22) Filed: Sep. 16, 2004

(65) Prior Publication Data

US 2005/0183174 P1 Aug. 18, 2005

(51) Int. Cl.
*A01H 5/00* (2006.01)

(52) U.S. Cl. ..... Plt./104

(58) Field of Classification Search ..... Plt./104
See application file for complete search history.

*Primary Examiner*—Anne Marie Grunberg
*Assistant Examiner*—Annette H Para
(74) *Attorney, Agent, or Firm*—Klarquist Sparkman LLP

(57) ABSTRACT

Shrub/climber rose plant having medium-sized, soft yellow blooms, vigorous growth, free and continuous flowering, and slightly fruity fragrance.

1 Drawing Sheet

Genus and species: *Rosa hybrida.*
Variety denomination: 'AUSchesnut'.

ORIGIN OF THE INVENTION

The present invention relates to a new and distinct variety of a shrub rose plant named 'AUSchesnut' which was originated by me by crossing the variety 'AUSgold' (Golden Celebration), U.S. Plant Pat. No. 8,688 with an unnamed, unpatented seedling.

BACKGROUND OF THE INVENTION

The primary objective of this breeding was to produce a free flowering and healthy variety rose, having arching growth with soft yellow blooms of an informal nature, and a subtle fruity fragrance.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Medium-sized, soft yellow blooms.
2. Growth of medium vigor.
3. Free and continuous flowering.
4. Slight fruity fragrance.

Asexual reproduction of this new variety by budding, as performed at Albrighton, England, shows that the foregoing and all other characteristics and distinctions come true to form and are established and transmitted through succeeding propagations.

Comparison with Parents

'AUSgold' has large, cupped, golden-yellow flowers on a medium shrub, compared with the medium sized soft yellow blooms of 'AUSchesnut'. The pollen parent has medium sized pink blooms.

Comparison with Similar Variety

'AUSpoly' (U.S. Plant Pat. No. 9,008) has more pointed petals, and is a shrub of moderate size, whereas 'AUSchesnut' is a large arching shrub, with paler yellow blooms.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—'AUSgold' (U.S. Plant Pat. No. 8,688).
*Pollen parent.*—Unnamed Seedling (Unpatented).

FLOWER

Observations made from plants commencing at one year of age grown in a garden environment at Albrighton, England.

Blooming habit: Continuous.
Bud:
*Size.*—About 4 cm long and 3 cm in diameter when the petals start to unfurl.
*Form.*—The bud form is pointed ovoid.

*Color.*—When sepals first divide, bud color is Green Group 143C. When half blown, the upper sides of the petals are Yellow Group 10B; and the lower sides of the petals are Yellow Group 9D.

*Sepals.*—Color: Upper surface: Yellow-Green Group 144A. Lower surface: Yellow-Green Group 145A. Length: 2.1 cm. Width: 2.6 cm. Shape: Awl-shaped. Surface texture: Upper surface: Pubescent. Lower surface: Smooth. There are three lightly appendaged sepals. There are three unappendaged sepals with canescent edges.

*Receptacle.*—Color: Yellow-Green Group 144B. Shape: Campanulate. Size: Medium, about 1.3 cm long×1 cm wide. Surface: Smooth.

*Peduncle.*—Length: Medium, averaging about 3.5 cm. Surface: Smooth. Color: Yellow-Green Group 144B. Strength: Strong.

Bloom:

*Size.*—Medium. Average open diameter is about 6.4 cm.

*Borne.*—Several together in rounded clusters of four to fourteen blooms.

*Stems.*—Strength: Normal. Average length is about 65 cm with a diameter of 0.8 cm.

*Form.*—When first open: Globular. Permanence: Outer petals curl back.

*Petalage.*—Number of petals under normal conditions: 121.

*Color.*—The upper sides of the petals are Yellow Group 8C at the outer part and Yellow Group 9A towards the base. The reverse sides of the petals are Yellow Group 8D at the outer part and Yellow Group 10A towards the base. The base of each petal is Yellow Group 9A. The major color on the upper side is Yellow Group 7D.

*Variegations.*—None.

*Discoloration.*—The general tonality at the end of the first day: Yellow Group 8B. At the end of the third day: Fading to Yellow Group 10C.

*Fragrance.*—Slight, fruity.

Petals:

*Texture.*—Satiny.

*Size.*—Width: 2.8 cm. Length: 4 cm.

*Surface.*—Rough.

*Shape.*—Narrow elliptical. Margin: Reflexing and flat. Inner petals undulating. Apex Shape: Rounded. Base Shape: Pointed.

*Arrangement.*—Quartered.

*Petaloids.*—None.

*Persistence.*—Petals hang on and dry.

*Lastingness.*—On the plant: Fair (about 4 days). As a cut flower: Short (about 3 days).

Reproductive parts:

*Stamens.*—Number: 6. Length: 5 mm. Anthers: Length: 3 mm. Color: Yellow-Orange Group 23A. Arrangement: Tucked in calyx. Filaments: Color: Yellow-Orange Group 23A. Length: 4 mm. Pollen: Color: Orange Group 26A.

*Pistils.*—Number: 34. Length: 10 mm. Styles: Color: Yellow Group 4D. Length: 9 mm. Stigmas: Color: Yellow Group 8A. Length: 1 mm. Hips: None observed.

PLANT

*Form.*—Shrub.

*Growth.*—Branching and of medium vigor.

*Age at maturity.*—Two years.

*Mature plant.*—Height: 1.2 m. Width: 1 m.

*Wood.*—Mature Stem: Average length: 60 cm. Average diameter: 9 mm. Internode distance: 7 cm.

*Rootstock.*—Dr. Huey in the United States. *Rosa dumetorum* 'Laxa' for the observed plants in the United Kingdom.

Foliage: Number of leaflets on normal mid-stem leaves: 7.

*Size.*—Medium. About 11.5 cm long×8 cm wide.

*Quantity.*—Average number leaves per flowering stem: 5.

*Color.*—New foliage: Upper side: Green Group 137D. Lower side: Green Group 138A. Old foliage: Upper side: Green Group 139A. Lower side: Green Group 137B.

Leaflets:

*Size.*—About 4.5 cm long×3.2 cm wide.

*Shape.*—Elliptic.

*Base shape.*—Obtuse.

*Apex shape.*—Acuminate.

*Texture.*—Leathery.

*Edge.*—Serrated.

*Serrations.*—Single and small.

*Petiole.*—Color: Green Group 143C.

*Petiole rachis.*—Color: Green Group 144C. Underside: Prickles.

*Auricle shape.*—Awl-shaped.

*Stipules.*—Length: 2.5 cm; bearded.

*Disease resistance.*—Resistant to both powdery and downy mildew, blackspot and rust under normal growing conditions.

*Pest resistance.*—Not tested.

*Vein color.*—Green Group 146B.

*Venation pattern.*—Net-veined.

Wood:

*New wood.*—Color: Yellow-Green Group 144A. Bark: Smooth.

*Old wood.*—Color: Yellow-Green Group 146A. Bark: Smooth.

Prickles:

*Quantity.*—On main canes from base: Many, 20 per 30 cm per stem length. On laterals from main canes: Many, 25 per 30 cm per stem length.

*Form.*—Hooked downward.

*Length.*—1.8 cm.

*Color when young.*—Greyed-Red Group 178A.

*Color when mature.*—Greyed-Red Group 180A.

Small prickles:

*Quantity.*—On main stalks: None. On laterals: 6 per 30 cm of stem.

*Color.*—When young: Greyed-Purple Group 183A. When mature: Greyed-Orange Group 172B.

Winter hardiness: Not tested.

I claim:

1. A new and distinct variety of rose plant of the shrub/climber class, substantially as herein shown and described, characterized particularly by its medium-sized, soft yellow blooms, vigorous growth, free and continuous flowering, and slight fruity fragrance.

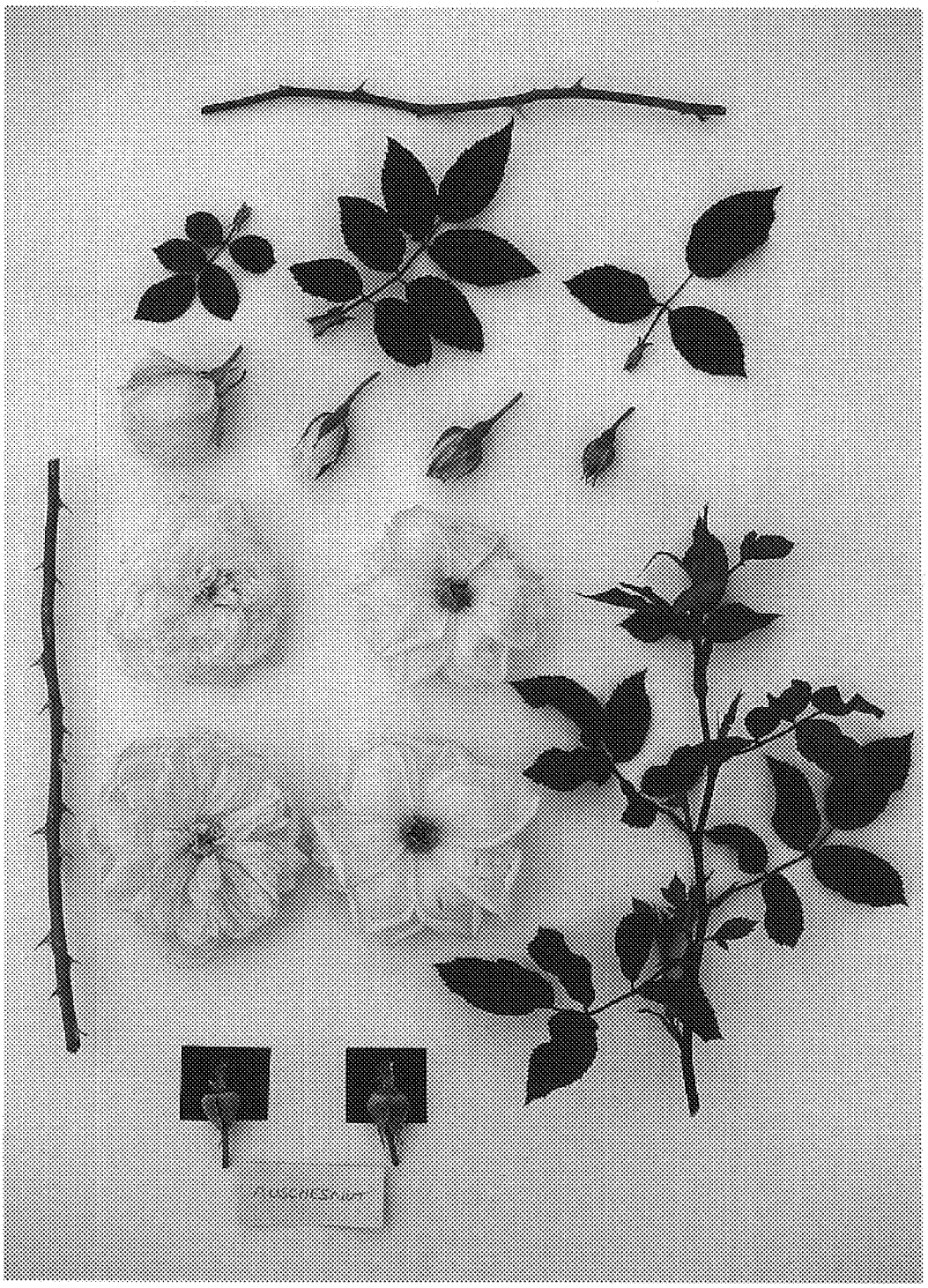

* * * * *